United States Patent
Sharma et al.

(10) Patent No.: US 12,357,747 B2
(45) Date of Patent: Jul. 15, 2025

(54) ENEMA DEVICE

(71) Applicant: CM Technologies, Inc., San Diego, CA (US)

(72) Inventors: Amit Kumar Sharma, New Delhi (IN); Nishith Chasmawala, Surat (IN); John Everett Martin, Gainesville, FL (US); Abhinav Ramani, Herndon, VA (US); Paul Thomas Hichwa, Mountain View, CA (US)

(73) Assignee: CM Technologies, Inc., San Diego, CA (US)

( * ) Notice: Subject to any disclaimer, the term of this patent is extended or adjusted under 35 U.S.C. 154(b) by 885 days.

(21) Appl. No.: 17/425,034

(22) PCT Filed: Jan. 22, 2020

(86) PCT No.: PCT/IB2020/050489
§ 371 (c)(1),
(2) Date: Jul. 22, 2021

(87) PCT Pub. No.: WO2020/152597
PCT Pub. Date: Jul. 30, 2020

(65) Prior Publication Data
US 2022/0118171 A1 Apr. 21, 2022

Related U.S. Application Data

(60) Provisional application No. 62/795,031, filed on Jan. 22, 2019.

(51) Int. Cl.
*A61M 3/02* (2006.01)

(52) U.S. Cl.
CPC ........ *A61M 3/0279* (2013.01); *A61M 3/0245* (2013.01); *A61M 2205/0238* (2013.01); *A61M 2205/3331* (2013.01)

(58) Field of Classification Search
CPC .............. A61M 3/0279; A61M 3/0287; A61M 3/0283; A61M 3/0245
See application file for complete search history.

(56) References Cited

U.S. PATENT DOCUMENTS 4,617,011 A * 10/1986 Bloxom, Jr. ........ A61M 3/0208
604/257
4,790,811 A * 12/1988 Bloxom, Jr. ........ A61M 3/0241
604/257

(Continued)

FOREIGN PATENT DOCUMENTS

WO 2009064718 A1 5/2009

OTHER PUBLICATIONS

International Search Report from PCT International Application No. PCT/IB2020/050489, dated May 26, 2020.

*Primary Examiner* — Sarah Al Hashimi
*Assistant Examiner* — Arjuna P Chatrathi
(74) *Attorney, Agent, or Firm* — Budzyn IP Law, LLC

(57) ABSTRACT

The invention comprises an enema device configured for fluid delivery and evacuation management—which includes a retaining component for retaining a part of the enema device within the rectum, coupled with a collection component for collecting stool or liquid discharge received from the rectum. The device may additionally include a fluid delivery component to enable delivery of enema fluid to the colon, and/or a withdrawal component to support safe removal of the device from the patient.

9 Claims, 9 Drawing Sheets

(56) References Cited

U.S. PATENT DOCUMENTS

| | | | | |
|---|---|---|---|---|
| 4,964,852 | A | * | 10/1990 | Dunning ............... F16K 15/148 |
| | | | | 222/525 |
| 2005/0087570 | A1 | * | 4/2005 | Jackman ................ B65D 47/10 |
| | | | | 222/541.4 |
| 2006/0110208 | A1 | * | 5/2006 | Tsaur .................... B65D 39/00 |
| | | | | 401/185 |
| 2010/0280489 | A1 | * | 11/2010 | Nishtala .............. A61M 3/0287 |
| | | | | 604/514 |
| 2016/0158423 | A1 | * | 6/2016 | Pigazzi ............... A61M 3/0212 |
| | | | | 604/35 |
| 2016/0206805 | A1 | * | 7/2016 | Hassidov ............. A61M 3/022 |
| 2018/0193551 | A1 | | 7/2018 | Zhou |
| 2018/0311480 | A1 | * | 11/2018 | Göbel .................. A61F 2/0013 |

* cited by examiner

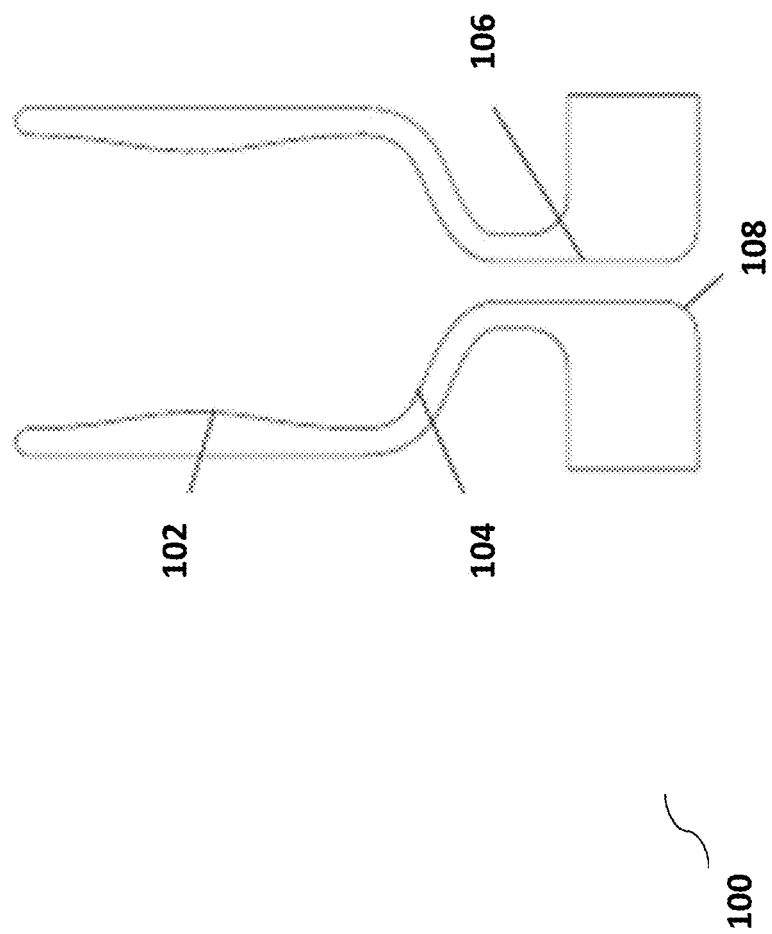

ENEMA DEVICE

CROSS-REFERENCE TO RELATED APPLICATIONS

This application is a National Stage Application under 35 U.S.C. § 371 of PCT Application No. PCT/IB2020/050489, filed Jan. 22, 2020, which claims priority from and the benefit of U.S. Provisional Patent Application No. 62/795,031 filed Jan. 22, 2019, which are hereby incorporated by reference in their respective entireties.

FIELD OF THE INVENTION

The invention relates to the domain of gastro-intestinal (GI) treatment and stool management, and provides enema devices for enabling delivery of enemas to patients and for simultaneously managing and collecting stool or liquid evacuated as a consequence of the enema procedure.

BACKGROUND

An enema is a medical procedure whereby fluid is injected into the rectum of a patient in order to induce bowel movement. The need for such a procedure typically arises in patients suffering from certain physical ailments in which voluntary bowel control is impaired.

Additionally, patients may receive medicated enemas for treatment of certain diseases such as inflammatory bowel disease or infections such as *Clostridium difficile*. Furthermore, fecal microbiota transplants, which involve the administration of healthy liquefied fecal matter into the colon, are becoming more common treatments for the same conditions.

Due to various factors such as traumas, diseases, age, or recent surgery, there are a number of people who are in need of these types of procedures, but are not able to move to a toilet for post-enema evacuation. For these groups of bed-ridden patients, enemas are normally performed while lying down on the bed and effluents are caught with diapers, pads, or bedpans. This causes stool to be exposed to the patient, care provider, and care environment, which is unhygienic and can increase the risk of infections and other complications. Furthermore, the cleaning of these patients and changing of diapers, clothing, and linens quickly becomes time consuming and an economic burden.

Additionally, current solutions for delivery of enema fluids to a patient's rectum present further challenges. While such solutions largely rely on enema catheters (comprising an indwelling component for positioning within the rectum, and a conduit connected to the indwelling component that enables enema fluid to be delivered to the rectum and for said enema fluid and rectal discharge to be subsequently evacuated from the subject's rectum) for delivering fluid into the rectum of the patient, it is also necessary to ensure that subsequent to delivery of the enema fluid into the rectum, the delivered fluid is retained in the rectum for a certain period of time—and is not permitted to immediately exit the rectum through the conduit(s) within the enema catheter. The current solutions to ensure fluid retention within the rectum typically involve the use of a secondary clip component that clamps shut a catheter-sheath (i.e. a transit sheath configured to enable fluid to transit through the catheter) or catheter fluid delivery conduit, at a location external to the patient's rectum (preferably just outside of the anal opening). By clamping the catheter-sheath or catheter fluid delivery conduit, the clamp prevents enema fluid from being evacuated from the patient's rectum. The enema fluid and fecal discharge from the patient's rectum is enabled subsequent to elapse of a suitable time period, by removing the clamp and re-opening the catheter-sheath or catheter fluid delivery conduit.

A significant disadvantage to use of clamps is patient safety. It has been found that when the rectum fills and pressure increases, a defecation response is triggered. The rectal tissue then contracts and the anal sphincters relax in order to expel the effluents. If a clamp has been used to clamp shut the evacuation passage (i.e. the catheter sheath or catheter fluid delivery conduit) and the patient's defecation response is strong, the entire device (i.e. both the indwelling component and the fluid conduit) may be unintentionally expelled from the rectum—resulting in involuntary expulsion of the enema fluid and the involuntary and unsanitary discharge of the contents of the patient's rectum.

The other disadvantage to this method is an increase in time and effort that a caregiver requires to dedicate to the enema process. In order for fluid retention procedures to be effective, the caregiver must remember to put on and take off the secondary clip at the required times. This is not only an extra set of tasks to remember, but are oftentimes considered tedious ones to perform. In cases where the patient is not fully conscious, maneuvering the patient to place the clips may also require the involvement of multiple caregivers.

An alternative solution known in the art for solving the problem of fluid retention involves the use of an inflatable balloon placed on the inside of catheter device at the proximal tip that resides inside of the patient. To inflate the balloon, the caregiver must attach an air-filled syringe to a port located outside of the patient and push air through a small lumen channel. The balloon inflates to press against the inside walls of the catheter lumen and blocks fluid from leaking into the lumen. Deflating the balloon requires the reverse process of attaching an empty syringe to the external port and drawing the air out of the balloon through the small lumen channel. The disadvantages described above in connection with the clamping mechanism also apply for this method.

There is accordingly a need for a device for delivering enemas to patients that addresses the above shortcomings.

SUMMARY

The invention comprises an enema device configured for fluid delivery and evacuation management—which includes a retaining component for retaining a part of the enema device within the rectum, coupled with a collection component for collecting stool or liquid discharge received from the rectum. The device may additionally include a fluid delivery component to enable delivery of enema fluid to the colon, and/or a withdrawal component to support safe removal of the device from the patient.

In an embodiment, the invention comprises a device for collection of fecal discharge, comprising (i) a retaining component configured for deployment within a subject's rectum and having an annular cross-section, (ii) a collection component comprising a flexible sheath defining a receptacle for collection of discharge from a subject's rectum, and an open first end and a second end, wherein the open first end of said collection component is coupled with the retaining component such that the annular cross-section of the retaining component defines a fluid passageway leading into the open first end of the collection component affixed or integrated with said retaining component, and (iii) at least one pressure sensitive fluid flow control component disposed between the retaining component and the second end of the collection component, configured to restrict fluid flow between the retaining component and the second end of the collection component at fluid pressures of less than 200 mmHg.

The pressure sensitive fluid flow control component may include an adherent coating having adhering characteristics and that is applied to one or more regions on internal surfaces of the flexible sheath.

In an embodiment the adherent coating comprises a gelatinous coating.

The adherent coating may be applied in an annular band on an inner periphery of the collection component at a constrained region of the collection component.

In a particular embodiment, the adherent coating is applied to the internal surfaces of the flexible sheath such that thickness of said adherent coating has a value of between 0 and 4 in terms of a NLGI consistency rating or has a value of between 205 and 385 in terms of a Worked Penetration Value.

The adherent coating may be selected so as to have viscosity of between 100 cSt and 1500 cST defined in terms of Base Oil Kinematic Viscosity.

In an embodiment, the adherent coating has tackiness of between 1N and 50N defined in terms of a Modified Probe Tack Test.

The invention additionally includes a fluid delivery component configured to deliver fluid from an external source to a subject's rectum when the retaining component is positioned within the rectum, the fluid delivery component comprising a fluid conduit having an open first end proximal to the retaining component, a second end distal to the retaining component and a lumen therebetween.

In an embodiment, the device may include a flow control component disposed within the fluid conduit of the fluid delivery component, wherein said flow control component is configured to allow fluid flow from the second end to the open first end, and to prevent fluid flow from the open first end to the second end.

In a specific embodiment of the device the fluid delivery component is affixed to at least one of the retaining component and the collection component.

BRIEF DESCRIPTION OF THE ACCOMPANYING DRAWINGS

FIGS. 1A and 1B illustrate portions of human rectal anatomy.

DETAILED DESCRIPTION

Figure 1B:
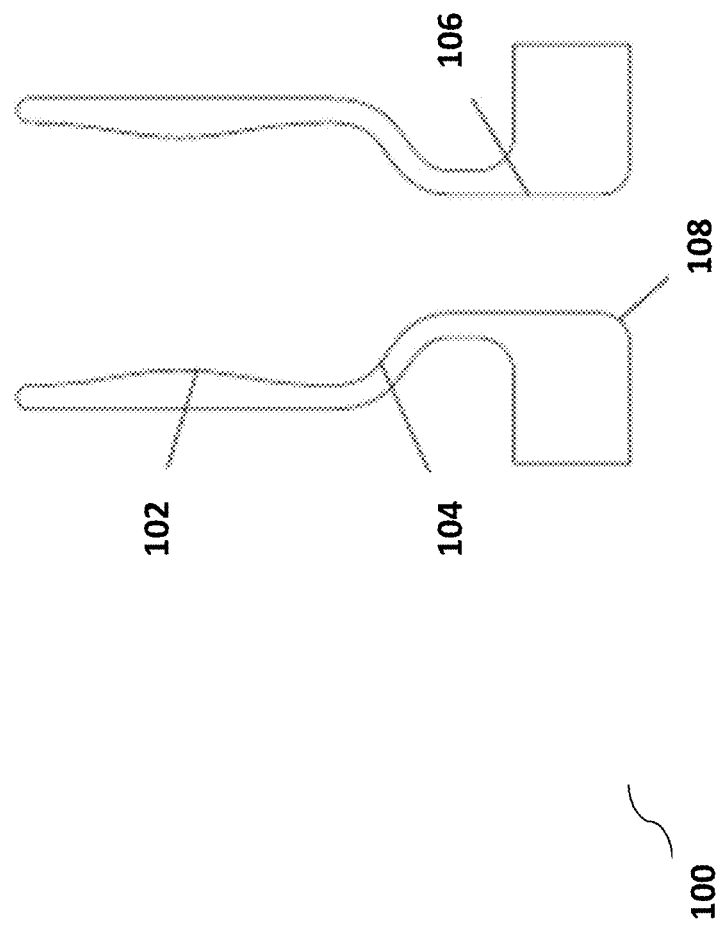

The invention comprises an enema device configured for fluid delivery and evacuation management—which includes a retaining component for retaining a part of the enema device within the rectum, coupled with a collection component for collecting stool or liquid discharge received from the rectum. The device may additionally include a fluid delivery component to enable delivery of enema fluid to the colon, and/or a withdrawal component to support safe removal of the device from the patient.

The invention may also include an insertion component to constrain the resilient component in a collapsed state during placement into the rectum.

As described in more detail below, the retaining component may comprise a flexible and resilient substantially "ring-like" structure defining a lumen or passage within the periphery thereof. The retaining component is caused by its resilient properties to naturally expand from a collapsed state having a small cross-sectional area to an expanded state having a larger cross sectional area. The resilient properties of the retaining component ensures that in an expanded configuration the retaining component presses against the rectal walls, causing the external peripheral surface(s) of the retaining component to resiliently conform to adjacent rectal walls and to ensure that a complete seal is created between the external periphery of the retaining component and the rectal walls—thereby ensuring that any enema fluid, stool or fecal discharge passes through the lumen of the retaining component instead of leaking through spaces between the external periphery and adjacent rectal walls.

The collection component (or transit sheath) comprises a bag, chute or tube made of a thin, low-friction, flexible, skin friendly material that has an open first end through which stool or fluid may enter said collection component. The first end of the collection component (which is an open end that is proximal to the subject's rectum) may be coupled with the retaining component such that stool or liquid discharge entering the lumen of the retaining component passes into the collection component through the open proximal end of said collection component. The collection component may be configured to hold and contain material that passes into it through the open proximal end. The other end of the collection component may in an embodiment be a closed end (for example a closed end that is distal to the subject's rectum), so as to ensure that the stool or liquid discharge is retained within the collection component.

The insertion component may take any number of different forms. In one, the insertion component is a type of obdurator that is able to be fragmented or disassembled, within which the retaining component is confined in a compressed state. The obdurator may be used to deliver the retaining component into a subject's rectum (in the compressed state), and the retaining component is thereafter released from confinement within the obdurator—thereby permitting it to transition to an expanded state. The obdurator is subsequently withdrawn from the rectum, while the expanded retaining component remains within the subject's rectum. Since the retaining component is coupled to the collection component, stool or fluid discharge from the rectum entering the retaining component transits into the collection component, which is at least partially positioned outside the rectum The fluid delivery component comprises an assembly configured to deliver fluid from an external source to the subject's rectum while the retaining component is positioned within the rectum. The fluid delivery component comprises a fluid conduit having an open proximal end, a distal end and a lumen connecting the two—and may in an embodiment comprise a length of tubing or piping of appropriate diameter. The fluid delivery component may be coupled with one or both of the retaining component and the collection component such that when the retaining component is positioned within a subject's rectum, the open proximal end is positioned within the subject's colon while the distal end lies outside of the rectum. The lumen connecting the two ends provides a fluid passageway that enables fluid to be delivered from the distal end through the open proximal end and to the subject's colon. As a result of the configuration, the fluid delivery component enables delivery of enema fluid into the subject's rectum once the retaining component has been positioned within the rectum.

The withdrawal component comprises a structure or assembly that is configured to change either or both of the orientation and/or cross-section of the retaining component to enable withdrawal of the retaining component from the rectum. In an embodiment discussed in this invention the withdrawal component and the fluid delivery component may comprise a single component.

Specific embodiments of the above are discussed in greater detail below.

FIG. 1A illustrates the relevant portions of the human rectum 100, including rectal walls 102, the anorectal junction 104, the anal canal 106, and the anal verge 108. In FIG. 1A, anal canal 106 is shown in a constricted position. FIG. 1B depicts the same portions of the rectal anatomy but with the anal canal 106 now in an expanded position (for example when the subject is passing stool).

Figure 2A:
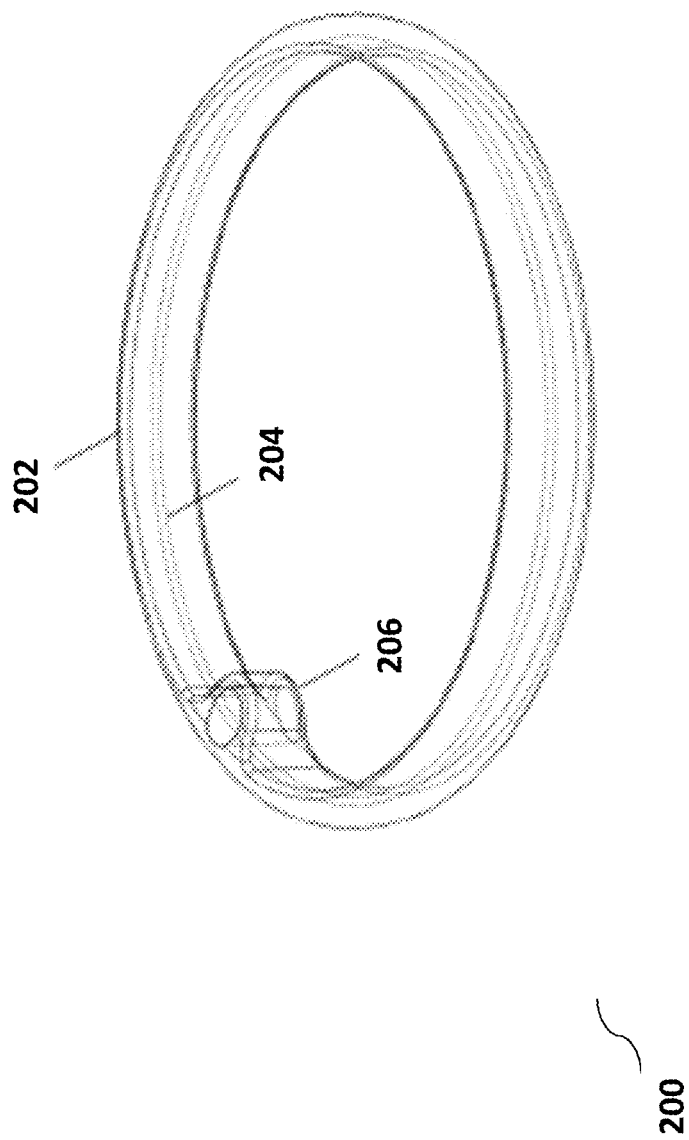
FIG. 2A illustrates an embodiment of a retaining component in an expanded state in accordance with the present invention.

FIG. 2A illustrates an embodiment of the retaining component 200 in an expanded state. Retaining component 200 comprises a pliant and collapsible annular body 202 comprising a first material, and a resilient ring 204 embedded within said annular body 202, said resilient ring 204 comprising a second material. Stated differently, the pliant and collapsible annular body 202 may be formed as an overlayer that completely covers or encapsulates resilient ring 204—such that both annular body 202 and resilient ring 204 are co-axially arranged. Annular body 202 may additionally include a port (or retaining cavity) 206 for housing or holding an end of the fluid delivery component—through which end, enema fluid may be delivered into a subject's rectum.

Owing to the fact that it is comprised of collapsible annular body 202 and a resilient ring 204 embedded therewithin, retaining component 200 can be collapsed into a number of different configurations to reduce its cross-sectional profile for the purposes of delivering it into a subject's rectum.

Figure 2B:
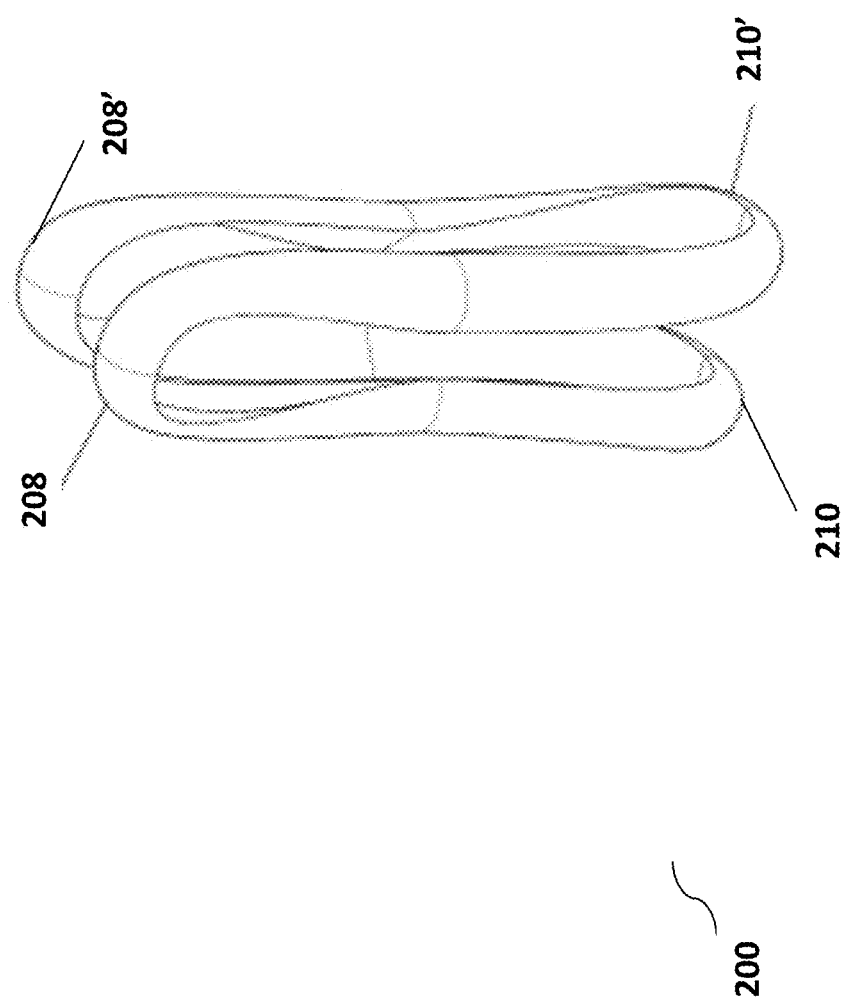
FIGS. 2B and 2C illustrate configurations in which the retaining component may be collapsed.

FIG. 2B illustrates a first exemplary configuration into which retaining component 200 can be collapsed—wherein in said collapsed state, retaining component 200 has been compressed and collapsed along two mutually perpendicular axes to form two peaks 208, 208' and two troughs 210, 210'.

Figure 2C:
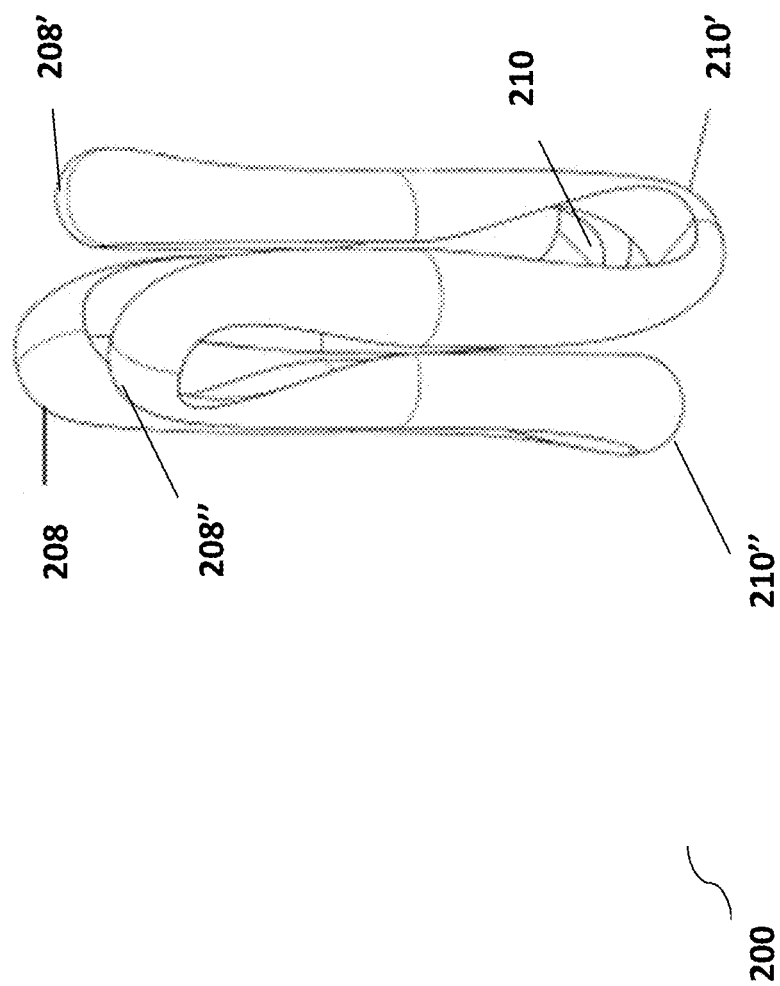

FIG. 2C illustrates a second exemplary configuration into which retaining component 200 can be collapsed—wherein in said collapsed state, retaining component 200 has been compressed and collapsed along three axes, each arranged with 120 degrees between them, to form three peaks 208, 208', 208" and three troughs 210, 210', 210".

It would be understood that the embodiments of FIGS. 2B and 2C are only exemplary and that retaining component 200 can be collapsed into any number of other compressed or collapsed configurations. However, it will be noted by comparing the embodiments of FIGS. 2B and 2C to the illustrated embodiment in FIG. 2A, that in its collapsed state, the cross-sectional profile of retaining component 200 is substantially reduced—enabling convenient insertion into and withdrawal from a subject's rectum.

Figure 3:
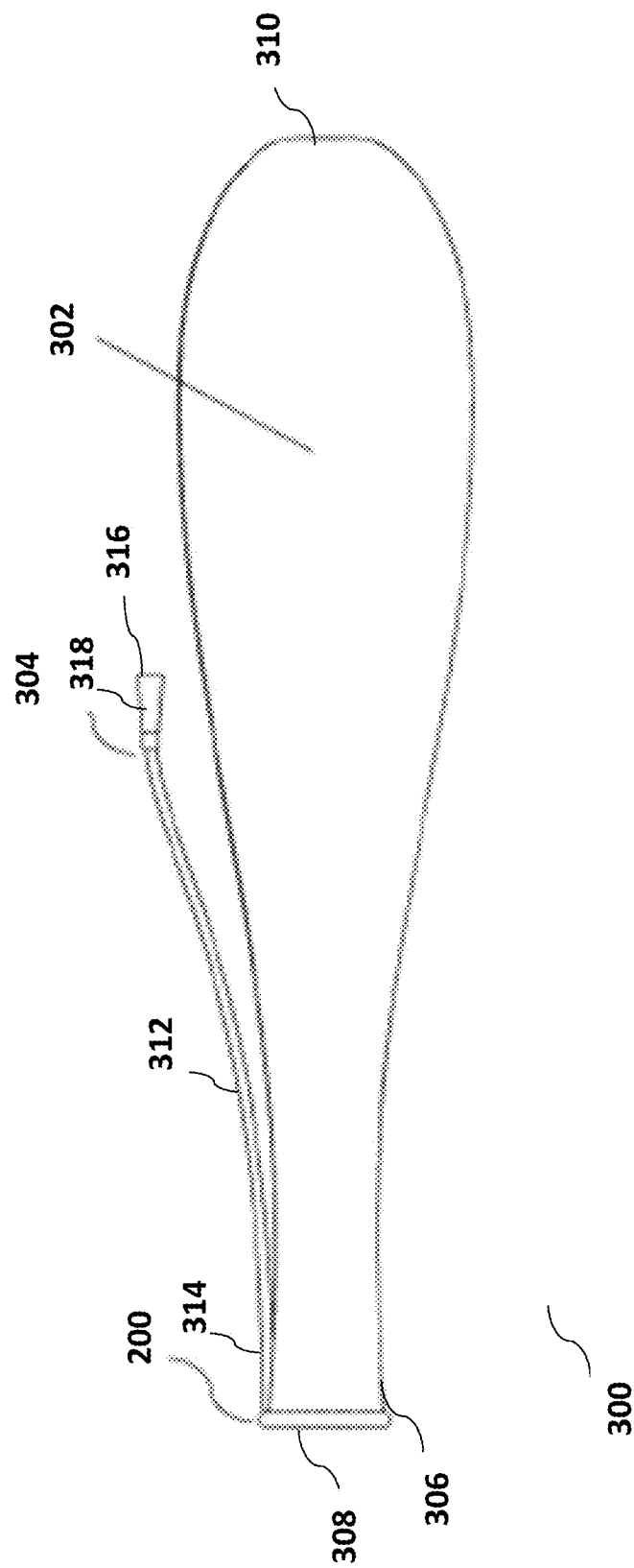
FIG. 3 illustrates an assembled enema device for fluid delivery and evacuation management in accordance with embodiments of the present invention.

FIG. 3 illustrates an assembled enema device 300 for delivery of enema fluid and for management or collection of fecal discharge and/or fluid discharge from the rectum, said enema device 300 comprising retaining component 200 for retaining a part of the device within the rectum, coupled with a collection component 302 for collecting stool or liquid discharge received from the rectum, and a fluid delivery component 304 for delivery of fluid to the colon. In the illustrated embodiment, and as discussed in further detail below, the fluid delivery component 304 also functions as a withdrawal component to support safe removal of the enema device 300 from a patient's rectum.

As illustrated in FIG. 3, collection component 302 comprises a bag (or alternatively a chute or tube) made of a thin, low-friction, flexible, skin friendly material that has an open first end 306 through which stool or fluid evacuated from a subject's rectum may enter said collection component 302. The open first end of collection component 302 may be coupled with retaining component 200 such that stool or liquid discharge entering an annular opening 308 formed by the retaining component 200, passes into the collection component 302 through first open end 306 of said collection component 302. The collection component 302 may be configured to hold and contain material that passes into it through the open proximal end. In an embodiment, this is achieved by ensuring that a second end 310 of collection component 302 is a closed end.

Also shown in FIG. 3 is fluid delivery component 304—which comprises an assembly configured to deliver fluid (for example enema fluid) from an external source to the subject's rectum while the retaining component 200 is positioned within the rectum. Fluid delivery component 304 comprises a fluid conduit 312 having a first open end 314 positioned proximal to retaining component 200 and a second open end 316 positioned distal to retaining component 200. As shown in FIG. 3, second open end 316 of fluid delivery component 304 may include a connector 318, which enables fluid delivery component 304 to be connected to a fluid source. Fluid from the fluid source may enter second open end 316, pass through fluid conduit 312 and be delivered into a subject's rectum through first open end 314 of fluid conduit 312. Referring back to FIG. 2A, in an embodiment of the invention, fluid conduit 312 or first open end 314 of said fluid conduit 312 may be housed or held within port (or retaining cavity) 206 of retaining component 200—which ensures that when retaining component 200 is disposed within a subject's rectum, first open end 314 of fluid conduit 312 is also disposed within the subject's rectum, thereby enabling fluid to be delivered to the subject's rectum or colon through fluid delivery component 304.

Figure 4:
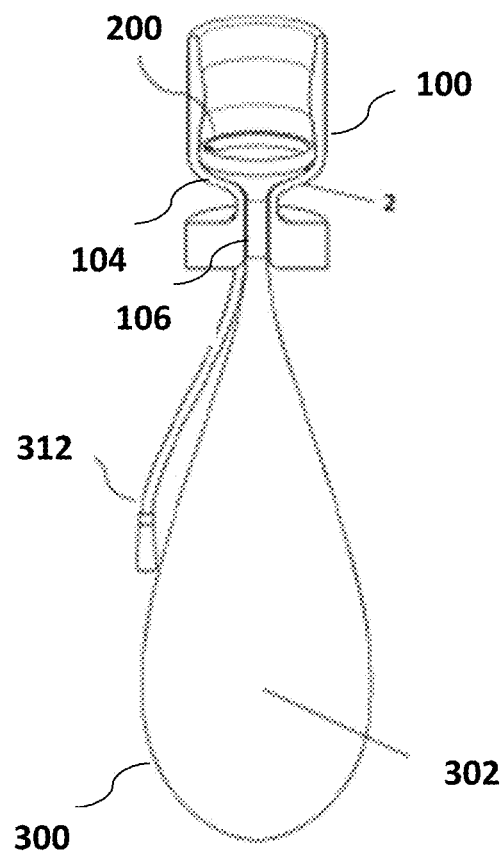
FIG. 4 illustrates an exemplary instance of an assembled enema device for fluid delivery and evacuation management, positioned within a patient's rectum.

FIG. 4 illustrates an exemplary instance of enema device 300 positioned within a patient's rectum 100. As shown in FIG. 4, retaining component 200 is positioned within the subject's rectum 100 above the shelf structure formed by the subject's anorectal junction 104. Owing to the distance between the walls of the rectum 100 above the anorectal junction 104, retaining component 200 has transitioned to its expanded state, and in its expanded state rests securely on the walls of the anorectal junction 104. Since the distance between the walls of the anal canal 106 beneath the anorectal junction are narrower than the expanded cross section of retaining component 200 in its expanded state, retaining component 200 is securely held by anorectal junction 104 and accidental withdrawal of retaining component 200 from the subject's rectum is prevented.

It would be understood that retaining component 200 may be delivered to a position above the anorectal junction 104 by compressing retaining component 200 into a configuration having a cross-section less than the cross-section of anal canal 106, delivering said retaining component 200 (while remaining in a compressed configuration) through anal canal 106 to a position above anorectal junction 104, and thereafter releasing retaining component 200 from the applied compressive forces—thereby allowing retaining component 200 to transition to its expanded state, in which expanded state, it naturally resists withdrawal through the narrower anal canal 106.

As shown in FIG. 4, first ends of collection component 302 and fluid delivery component 304 (each of which have an end affixed to or in proximity to retaining component 200), respectively trail said retaining component 200 into the rectum, while opposite ends of said collection component 302 and fluid delivery component 304 pass through anal canal 106 and are located outside of rectum 100. Once retaining component 200 of enema device 300 is delivered into and securely positioned within the subject's rectum, enema fluid may be delivered to the rectum through fluid delivery component 304.

Figure 5:
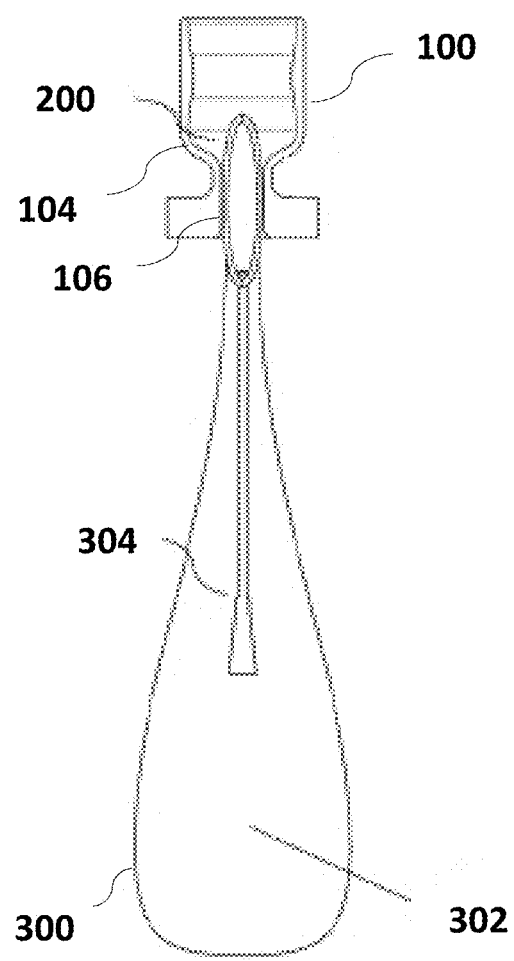
FIG. 5 illustrates an exemplary instance of withdrawal of an assembled enema device for fluid delivery and evacuation management from within a patient's rectum.

FIG. 5 illustrates an exemplary instance of withdrawal of enema device 300 from within a patient's rectum—which withdrawal is achieved by removing retaining component 200 from the rectum.

As in the case of insertion, removal of retaining component 200 (and consequently of device 300) from a subject's rectum requires application of forces that cause retaining component to transition from an expanded state to a compressed state having an orientation or cross-section sufficient to enable retaining component 200 to be withdrawn through anal canal 106 by application of withdrawing force. In an embodiment, retaining component 200 may be caused to change orientation or collapse into a sufficiently compressed state to enable withdrawal through anal canal 106 by application of (i) withdrawing force (in a direction distal to the rectum) at a plurality of points distributed around a periphery of retaining component 200 (which withdrawing force may be applied by one or more tethers provided on the periphery of retaining component 200)—which causes retaining component 200 to collapse or transition to a collapsed state, whereinafter continued application of withdrawing force in a direction distal to the rectum causes retaining component 200 (and device 300 as a whole) to be withdrawn from the subject's rectum.

In the embodiment illustrated in FIG. 5, the withdrawing force on retaining component 200 is applied through fluid delivery component 304, by applying a withdrawing force on said fluid delivery component 304 in a direction distal to the rectum. Since fluid delivery component is connected at one end with retaining component 200, application of the withdrawing force on fluid delivery component 304 results in retaining component being drawn into anal canal 106 starting from the point of connection between fluid delivery component 304 and retaining component 200—which forces retaining component 304 to be compressed and drawn through anal canal 106 and out of the subjects' rectum.

As with prior art devices, there is a need to provide a solution wherein enema fluid that is delivered to the subject's rectum is retained within the rectum for a desired interval of time, and is prevented from being untimely evacuated. The invention seeks to address this requirement without subjecting patient's to the serious shortcoming in other prior art devices that rely on clamping devices or balloon devices to ensure that enema fluid that is delivered to the subject's rectum is retained within the rectum for a desired interval of time.

The invention addresses the requirement for retaining enema fluid that is delivered to the subject's rectum for a desired interval of time, without risking involuntary expulsion of enema device 300 by implementing two separate flow control components.

The first flow control component comprises a directional flow control valve incorporated within fluid delivery component 304, and which permits for delivery of enema fluid or other fluid through fluid delivery component from open second end 316 through fluid conduit 312 and out of first open end 314 into the subject's rectum, while preventing fluid flow in the reverse direction—i.e. preventing fluid flow from first open end 314 towards seconds second open end 316. The invention may achieve this through any single direction flow controller—for example through a one-way check valve, located anywhere within fluid delivery component 304 between open second end 316 and open first end 314. By implementing a single direction flow controller that only permits for fluid flow from second open end 316 to first open end 314, fluid delivery component 304 ensures that fluid delivered to the rectum and/or fecal discharge from the rectum cannot be evacuated or allowed to escape through fluid delivery component 304.

The second flow control component comprises a pressure sensitive fluid flow control component located between retaining component 200 and a second end 310 of collection component 302 that is distal to retaining component 200. The pressure sensitive fluid control component may comprise a pressure actuatable valve or seal that prevents fluid flow from a subject rectum into collection component 200 up to a certain defined or rated fluid pressure, and once the fluid pressure within the subject's rectum exceeds the defined or rated fluid pressure, the pressure actuatable valve opens and allows fluid to be evacuated from the subject's rectum, through retaining component 200 and into collection component 302.

By implementing a pressure actuatable valve as a flow control component, the invention offers multiple advantages, including (i) ensuring that enema fluid delivered to a subject's rectum is not immediately drained into collection component 304, and instead is retained in the rectum until the subject's defecation response to the enema fluid is sufficiently strong to evacuate the enema fluid and contents of the subject's rectum through the fluid path that is controlled by the pressure actuatable valve, (ii) ensuring that the retaining component is not inadvertently expelled from the rectum in cases where a patient's defecation response is strong, since in such case the strong defecation response would result in fluid pressure within the rectum exceeding the defined pressure threshold of the pressure actuatable valve, resulting in the pressure actuatable valve transitioning into an open position and allowing enema fluid and fecal discharge to be evacuated from the subject's rectum and into collection component 304, and (iii) thereby avoiding the necessity of human supervision throughout the enema process—since the human caregiver now simply has to deliver and correctly position the retaining component 200 within the subject's rectum.

Figure 6:
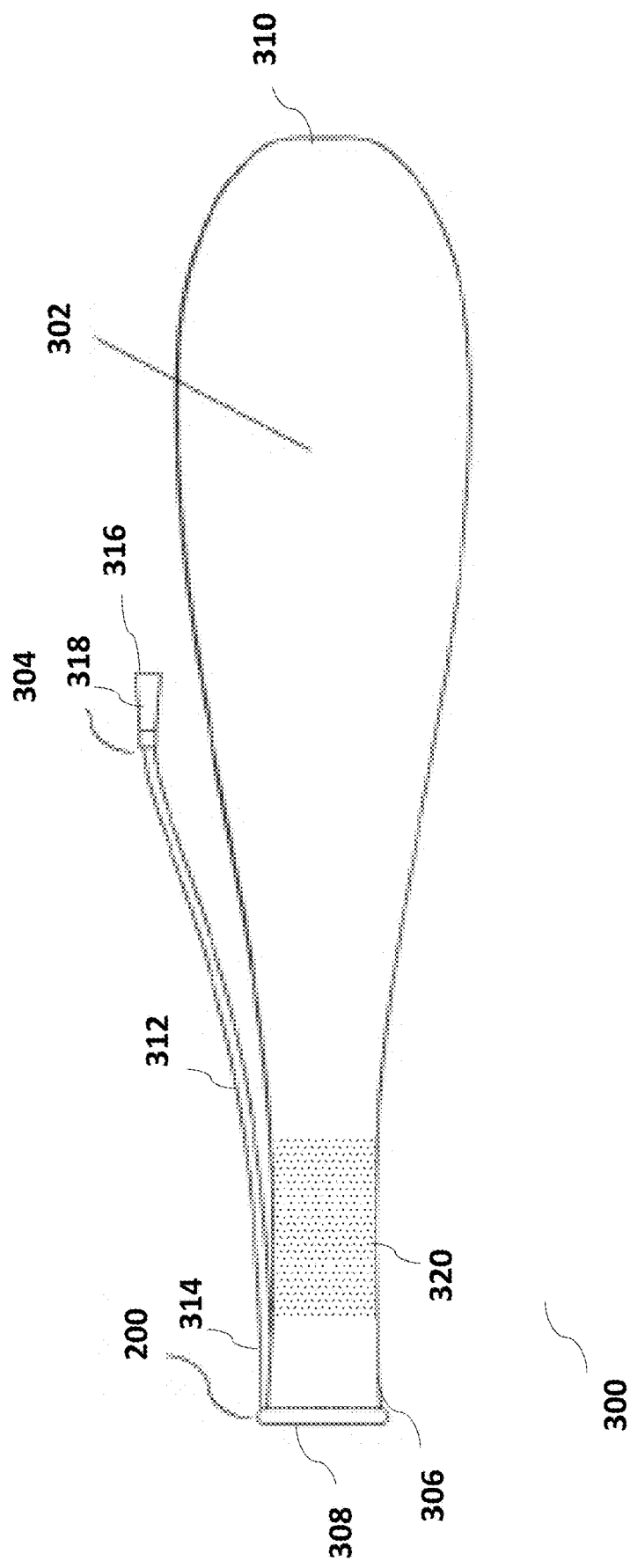
FIG. 6 illustrates a flow control component within an assembled enema device for fluid delivery and evacuation management.

FIG. 6 illustrates a particular embodiment of the second flow control component comprising a pressure sensitive fluid flow control component located between retaining component 200 and a second end 310 of collection component 302 that is distal to retaining component 200. In the illustrated embodiment, the pressure sensitive fluid flow control component comprises an adherent coating comprising a soft, conforming material having adhesive or sticky or tacky properties, that is applied in a band (or at a region) 320 around an inner peripheral surface of collection component 302—in an embodiment (as shown in FIG. 6) at a constrained area of the inner periphery of collection component having a diameter that is less than the diameter of an inner periphery of the collection component 302 at its widest point. In a particular embodiment illustrated in FIG. 6, the constrained area at which the material having adhesive, sticky or tacky properties is located proximal to the open first end of collection component 302 (that is coupled to retaining ring 200) and distal to the second end of collection component 302.

The adherent coating may be any sticky, rubbery, grease-like, viscous, tacky, or glutinous layer or coating, which may be solid, semi-solid, or substantially homogenous substance, and may optionally have a gelatinous, gel-like or jelly like character. Non-limiting examples may include a petroleum jelly, grease, a hydrogel or hydrocolloid material.

As a result of its adherent properties, the adherent coating causes formation of a physical barrier at band or region 320 inside of the flexible sheath—and preventing passage of fluid or particulate matter through said band or region 320. The adherent coating achieves this by holding the inner periphery of the flexible sheath of collection component 302 substantially closed at band or region 320—which prevents passage of fluid or particulate matter through the band or region 320. In effect the adherent coating forms a seal at band or region 320 by holding together the inner surfaces of the collection component 302 at band or region 320—thereby closing passage into collection component 302. In case the closure formed by the adherent coating is not a perfect seal, gaps that remain between the inner surfaces of the collection component 302 within band or region 320 are simultaneously physically closed due to the adherent coating itself filling up such gaps and physically blocking passage of liquid and/or particulate matter into collection component 302.

The adherent coating functions as a pressure sensitive fluid flow control component for the reason that when fluid pressure within the subject's rectum exceeds a certain threshold, the pressure exerted by the fluid/matter evacuated from the subject's rectum overcomes the holding forces exerted by the adherent coating on the inner surfaces of collection component 302 at band or region 320, causing said inner surfaces to separate and creating a fluid passage between retaining component 200 and a second end of the collection component 302 that is distal or retaining component 302—thereby allowing fluid and/or fecal matter evacuated from the subject's rectum to pass into collection component 302.

It has been discovered that the adherent coating is necessarily required to be selected to be strong enough to maintain closure of band or region 320 (and thereby retain enema fluid within the rectum) for sufficient time to enable enema fluids to act as intended within the subject' rectum, while at the same time to be weak enough to allow closure of band or region 320 to open in response to any defecation response or rectal evacuation response that is ordinarily anticipated after the enema fluids have had sufficient time to act within the subject's rectum or in response to fluid pressure that is sufficient to expel retaining component 200 from the subject's rectum in case the closure does not open.

It has been found that there are five main variables that are responsible for (and which require to be optimized) to achieve the operational functionality of the adherent coating.

Thickness: The thickness of the adherent coating is directly related to the density of the material, which alters the amount of pressure required to physically push the adherent coating from one location to another, or conversely to move the adherent coating out of the way. Thickness of the adherent coating may be defined according to the National Lubricating Grease Institute (NLGI) Consistency Rating (also called NLGI Grade), tested under ISO 6743 or ASTM D4950, and reported as 000, 00, 0 or integers up to 6. Thickness may be defined more specifically by Worked Penetration Value (also called Cone Penetration Value), tested under ASTM D217, ASTM D937, or ASTM D1403 and reported as integers. In embodiments of the invention, the thickness of the adherent coating applied at band or region 320 may be defined in terms of the NLGI Consistency Rating as having a value of between 0 and 4, or may be defined in terms of Worked Penetration Values as having a value, measure in tenth of a millimeter, between 385 and 175.

Viscosity: Viscosity is a measure of the forces that hold the molecules of a material to each other, so a higher viscosity will mean a higher force or pressure will be needed to separate the molecules. Viscosity is normally defined by Base Oil Kinematic Viscosity, tested under ASTM D445, ASTM D1084, ASTM D2196, ASTM D2983, or ISO 3104 and reported in centistokes or centipoise. In embodiments of the invention, the viscosity of the adherent coating may be defined in terms of Base Oil Kinematic Viscosity as having a value between 100 cSt and 1500 cSt at 40° C.

Tackiness: tackiness may be understood as a measure of the amount of deformation a viscous material can undergo before it breaks apart or separates, which is similar to viscosity but not the same. It has to do with how much "stretch" a certain amount of material can undergo before a separation occurs, but not the force required to create that stretch. In another sense, tackiness relates to how strong the material can attach to a surface, which will depend on the surface properties combined with the material properties and how they interact. Tackiness for grease materials or adherent materials does not have an internationally recognized standard definition. Though test methods such as String Length, Rotating Disk, Ductless Siphon, and Modified Probe have all been discussed in literature, none have determined as the gold-standard for determining grease tackiness. For the purpose of this description tackiness of the adherent coating may be defined by a Modified Probe Tack Test, with specific methodologies developed by Stanhope-Seta Ltd., and tested with the Seta Tack Tester. In embodiments of the invention, the adherent coating is selected to have tackiness properties such that test results from the Modified Probe Tack Test may be between 1N and 50N.

Volume: Volume of the adherent coating that is applied to the band or region 320 within collection component 302 has been found to be directly related to how much material the fluid would have to move in order to break through.

Stiffness: Stiffness of the material of the flexible sheath used for collection component 302 also has a consequence on the amount of force or pressure needed to move the sheath from one orientation to another (i.e.

from a closed state to an open one). Stiffer materials have been found to require more force to deform, while less stiff materials have been found to require less force. As the materials used for the flexible sheath are thin-films, there is no measured "flexural modulus" to reference for most of the materials that would normally be used in this application.

The functional characteristics of embodiments of the adherent coating may be defined in terms of the following two test methods, which replicate the intended use-case conditions.

Test Method 1, Static Lumen Seal Test: This test is performed by spreading 5 mL of the adherent coating along the inside surface of a 42 mm diameter layflat thermoplastic film of approximately 100-micron thickness for a length of 50 mm. The section of film with the adherent coating is subsequently folded into a "W" shaped cross-section and threaded through static tubes of 40 mm length with varying diameters. Pressure is applied to the internal section of the layflat tube from one side, starting from 10 mmHg.

Pressure is increased in increments of 5 mmHg every 10 seconds until the seal is broken and the pressure drops more than 10 mmHg. The maximum pressure is recorded as the Seal Pressure. Using this method, a relationship between lumen diameter (LD) and seal pressure (SP) is created, following approximately any of the below equations.

Exponential Equation: $SP(LD) = c1 e^{-c2*LD}$, where c1 and c2 are constants.

Power Equation: $SP(LD) = c1*LD^{c2}$, where c1 and c2 are constants.

Polynomial Equation: $SP(LD) = c1*LD^2 + c2*LD + c3$, where c1, c2, and c3 are constants.

In an embodiment of the invention wherein an adherent coating in accordance with the teachings of the present invention has been applied to a collection component in a band or region having a lumen diameter of 12 mm, the resulting seal pressure testing in accordance with Test Method 1 would be between 50 mmHg and 200 mmHg.

Test Method 2, Pressurized Lumen Seal Test: This test is performed by spreading 5 mL of the adherent coating along the inside surface of a 42 mm diameter layflat thermoplastic film of approximately 100-micron thickness for a length of 50 mm. The section of film with the adherent coating is subsequently folded into a "W" shaped cross-section and threaded through proxy or phantom anal canal fixtures. These fixtures are created by using a rigid tube of 30 mm to 40 mm diameter and 30 mm to 40 mm length with balloons fixed to the internal surface such that upon inflation, inwardly directed radial pressure is placed on the film in the location of the adherent coating. The pressure used in the balloon must be within 5 mmHg of the balloon material's modulus of elasticity to ensure the pressure of the balloon does not increase during the test. Pressure is applied to the internal section of the layflat tube from one side, starting from 10 mmHg. Pressure is increased in increments of 5 mmHg every 10 seconds until the seal is broken and the pressure drops more than 10 mmHg. The maximum pressure is recorded as the Seal Pressure. Using this method, a relationship between radial pressure (RP) and seal pressure (SP) is created, following approximately the following equation: $SP(RP) = c1*RP + c2$, where c1 and c2 are constants.

In an embodiment of the invention wherein an adherent coating in accordance with the teachings of the present invention has been applied to a collection component in a band or region, the resulting seal pressure using a radial pressure of 35 mmHg may be between 20 mmHg and 100 mmHg.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment that is specifically contemplated, the invention is intended to be practiced in the absence of any one or more element which are not specifically disclosed herein.

What is claimed is:

1. A device for collection of fecal discharge, comprising:
a retaining component configured for deployment within a subject's rectum and having an annular cross-section;
a collection component comprising a flexible sheath defining a receptacle for collection of discharge from a subject's rectum, and an open first end and a second end, wherein the open first end of said collection component is coupled with the retaining component such that the annular cross-section of the retaining component defines a fluid passageway leading into the open first end of the collection component affixed or integrated with said retaining component; and
at least one pressure sensitive fluid flow control component disposed between the retaining component and the second end of the collection component, wherein:
the pressure sensitive fluid flow control component is a pressure actuatable seal that:
prevents fluid flow from the subject's rectum into the collection component, at fluid
pressure less than defecation response pressure; and
permits fluid flow from the subject's rectum into the collection component, at fluid
pressure above defecation response pressure;
the pressure actuatable seal prevents fluid flow out from the subject's rectum into the collection component at fluid pressure less than defecation response pressure by holding together inner surfaces of the collection component;
fluid pressure above defecation response pressure separates the inner surfaces of the collection component and creates a fluid passage that allows fluid flow out from the subject's rectum into the collection component; and
wherein the pressure sensitive fluid flow control component comprises an adherent coating having adhering characteristics and that is applied to one or more regions on the inner surfaces of the collection component, such that:
the adherent coating holds together the inner surfaces of the collection component at fluid pressure below defecation response pressure; and
the adherent coating permits the inner surfaces of the collection component to separate at fluid pressure above defecation response pressure.

2. The device for collection of fecal discharge as claimed in claim 1, wherein the adherent coating comprises a gelatinous coating.

3. The device for collection of fecal discharge as claimed in claim 1, wherein the adherent coating is applied in an annular band on an inner periphery of the collection component at a constrained region of the collection component.

4. The device for collection of fecal discharge as claimed in claim 1, wherein the adherent coating is applied to the inner surfaces of the collection component such that thickness of said adherent coating has a value of between 0 and 4 in terms of a NLGI consistency rating or has a value of between 205 and 385 in terms of a Worked Penetration Value.

5. The device for collection of fecal discharge as claimed in claim 1, wherein the adherent coating has viscosity of between 100 cSt and 1500 cST defined in terms of Base Oil Kinematic Viscosity.

6. The device for collection of fecal discharge as claimed in claim 1, wherein the adherent coating has tackiness of between 1N and 50N defined in terms of a Modified Probe Tack Test.

7. The device for collection of fecal discharge as claimed in claim 1, comprising a fluid delivery component configured to deliver fluid from an external source to a subject's rectum when the retaining component is positioned within the rectum, the fluid delivery component comprising a fluid conduit having an open first end proximal to the retaining component, a second end distal to the retaining component and a lumen therebetween.

8. The device for collection of fecal discharge as claimed in claim 7, comprising a flow control component disposed within the fluid conduit of the fluid delivery component, wherein said flow control component is configured to allow fluid flow from the second end to the open first end, and to prevent fluid flow from the open first end to the second end.

9. The device for collection of fecal discharge as claimed in claim 7, wherein the fluid delivery component is affixed to at least one of the retaining component and the collection component.

* * * * *